United States Patent [19]

Uchida et al.

[11] Patent Number: 4,603,217

[45] Date of Patent: Jul. 29, 1986

[54] ESTER SUBSTITUTED ALKYL-2-(2,6-DICHLOROANILINO)PHENYL ACETATES

[75] Inventors: Katsuhiro Uchida, Kyoto; Mitsuo Mimura, Otsu; Shozo Masumoto, Shiga; Makoto Okumura, Moriyama; Masao Tohno, Otsu; Misako Matsumura, Shiga, all of Japan

[73] Assignee: Kaken Pharmaceutical Co., Ltd., Tokyo, Japan

[21] Appl. No.: 634,252

[22] Filed: Jul. 25, 1984

[30] Foreign Application Priority Data

Jul. 27, 1983 [JP] Japan ................................ 58-137188

[51] Int. Cl.$^4$ ......................................... C07C 101/453
[52] U.S. Cl. ..................................... 560/44; 548/500
[58] Field of Search .......................... 560/44; 548/500

[56] References Cited

U.S. PATENT DOCUMENTS 4,165,428  8/1979  Noda et al. ........................ 548/500

Primary Examiner—Glennon H. Hollrah
Assistant Examiner—D. B. Springer
Attorney, Agent, or Firm—Armstrong, Nikaido, Marmelstein & Kubovcik

[57] ABSTRACT

A novel anti-inflammatory drug, which exhibits rapidly a pharmacological activity, maintains the activity for a long time, and is free from a side effect such as a gastrointestinal disorder or a central nervous disturbance is disclosed.

The drug comprises a compound of an alkylcarbonyloxyalkylester or alkenylcarbonyloxyalkylester derivative of indolylacetic acid or anilinophenylacetic acid.

The compound is prepared by an esterification reaction.

10 Claims, No Drawings

ESTER SUBSTITUTED ALKYL-2-(2,6-DICHLOROANILINO)PHENYL ACETATES

BACKGROUND OF THE INVENTION

The present invention relates to a novel ester derivative of a substituted acetic acid having an excellent pharmacological activity and the process for preparing the same.

Hitherto, indomethacin (hereinafter referred to as IM) and diclofenac (hereinafter referred to as DF) have been broadly used as an acid nonsteroidal anti-inflammatory drug for a clinical use. IM and DF have a strong anti-inflammatory action, and are regarded as a first choice drug among other nonsteroidal anti-inflammatory drugs when used as an antirheumatic drug. However, both IM and DF have unfavorable side effects, for instance, a gastrointestinal disorder such as a loss of appetite, a nausea, a vomiting, a stomachache or an ulcer; and the like. Further, as for IM, it has another unfavorable side effects, for instance, a central nervous disturbance such as a headache, a sleepiness or a giddiness; and the like. Therefore, they are used restrictedly from the clinical viewpoint in spite of their strong therapeutic effect. Consequently, in case that IM or DF is administered to a rheumatic patient in need of a continuous IM- or DF-administration for a long period, especially a patient having a gastrointestinal disorder or a central nervous disturbance, there is a possibility that a use or an administration of IM or DF cannot but be limited or stopped from the reason described above. Moreover, its use or administration to the physical weak such as the aged or an infant is also restricted owing to its strong side effects.

As mentioned above, with respect to an acid nonsteroidal anti-inflammatory drug, there is a serious problem that it has a disadvantageous side effect such as a gastrointestinal disorder or a central nervous disturbance. Consequently, it is desired that an anti-inflammatory drug having an excellent pharmacological activity and reduced side effects is developed.

It is an object of the present invention to prepare an anti-inflammatory drug, which exhibits rapidly a pharmacological activity in man and maintains the activity for a long time, having a reduced side effect, e.g. a gastrointestinal disorder or a central nervous disturbance that is a drawback of a conventional acid nonsteroidal anti-inflammatory drug and, therefore, a wide safety margin.

Another object of the invention is to provide a process for preparing the above-mentioned drug.

These and other objects of the present invention will become apparent from the description hereinafter.

SUMMARY OF THE INVENTION

In accordance with the present invention, there is provided a compound of the general formula (I):

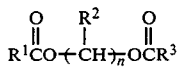

wherein $R^1$ is an indolylmethyl group of the formula (1):

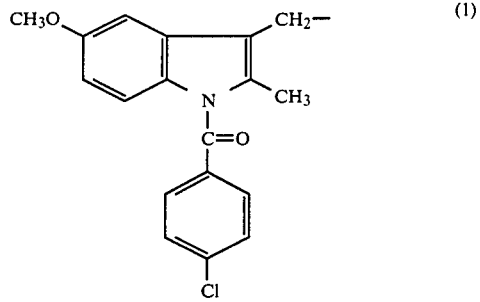

or an anilinophenylmethyl group of the formula (2):

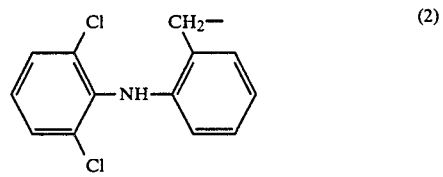

n is 1 or 2, $R^2$ is hydrogen atom or a lower alkyl group having 1 to 3 carbon atoms when n is 1, $R^2$ is hydrogen atom when n is 2 and $R^3$ is an alkyl group having 1 to 15 carbon atoms or an alkenyl group having 2 to 15 carbon atoms.

The compound of the present invention of the general formula (I) is an alkylcarbonyloxyalkylester or alkenylcarbonyloxyalkylester derivative of indolylacetic acid or anilinophenylacetic acid.

The present invention also provides a process for preparing the compound of the general formula (I).

DETAILED DESCRIPTION

Typical examples of the compound of the present invention of the general formula (I) are, for instance, as follows:

Compound 1: Crotonoyloxymethyl[1-(p-chlorobenzoyl)-5-methoxy-2-methyl-3-indolyl]acetate, Compound 2: 3,3-Dimethylacryloyloxymethyl[1-(p-chlorobenzoyl)-5-methoxy-2-methyl-3-indolyl]acetate, Compound 3: 2-(Acetoxy)ethyl[1-(p-chlorobenzoyl)-5-methoxy-2-methyl-3-indolyl]acetate, Compound 4: 2-(Crotonoyloxy)ethyl]1-(p-chlorobenzoyl)-5-methoxy-2-methyl-3-indolyl]acetate, Compound 5: 2-(3,3-Dimethylacryloyloxy)ethyl[1-(p-chlorobenzoyl)-5-methoxy-2-methyl-3-indolyl]acetate, Compound 6: 2-(2,4-Hexadienoyloxy)ethyl[1-(p-chlorobenzoyl)-5-methoxy-2-methyl-3-indolyl]acetate, Compound 7: 2-(3,7-Dimethyl-2,6-octadienoyloxy)ethyl[1-(p-chlorobenzoyl)-5-methoxy-2-methyl-3-indolyl]acetate, Compound 8: 1-(Acetoxy)ethyl[1-(p-chlorobenzoyl)-5-methoxy-2-methyl-3-indolyl]acetate, Compound 9: 1-(Propionyloxy)ethyl[1-(p-chlorobenzoyl)-5-methoxy-2-methyl-3-indolyl]acetate, Compound 10: 1-(Crotonoyloxy)ethyl[1-(p-chlorobenzoyl)-5-methoxy-2-methyl-3-indolyl]acetate, Compound 11: 1-(3,3-Dimethylacryloyloxy)ethyl[1-(p-chlorobenzoyl)-5-methoxy-2-methyl-3-indolyl]acetate, Compound 12: 1-(2,4-Hexadienoyloxy)ethyl[1-(p-chlorobenzoyl)-5-methoxy-2-methyl-3-indolyl]acetate,
Compound 13: Crotonoyloxymethyl-2-(2,6-dichloroanilino)-phenylacetate,
Compound 14: 3,3-Dimethylacryloyloxymethyl-2-(2,6-dichloroanilino)phenylacetate,
Compound 15: 2,4-Hexadienoyloxymethyl-2-(2,6-dichloroanilino)phenylacetate,
Compound 16: 2-(Acetoxy)ethyl-2-(2,6-dichloroanilino)-phenylacetate,
Compound 17: 2-(3,3-Dimethylacryloyloxy)ethyl-2-(2,6-dichloroanilino)phenylacetate,
Compound 18: 1-(Acetoxy)ethyl-2-(2,6-dichloroanilino)-phenylacetate,
Compound 19: 1-(Crotonoyloxy)ethyl-2-(2,6-dichloroanilino)phenylacetate,
Compound 20: 1-(3,3-Dimethylacryloyloxy)ethyl-2-(2,6-dichloroanilino)phenylacetate,
Compound 21: 1-(2,4-Hexadienoyloxy)ethyl-2-(2,6-dichloroanilino)phenylacetate, and the like.

The compound of the present invention is not limited to the exemplified compounds.

The compound of the present invention is prepared by an esterification reaction in which an alkylcarbonyloxyalkyl halide or alkenylcarbonyloxyalkyl halide of the general formula (II):

wherein X is a halogen atom and n, $R^2$ and $R^3$ are as defined above, is reacted with a compound selected from the group consisting of a compound of the general formula (3):

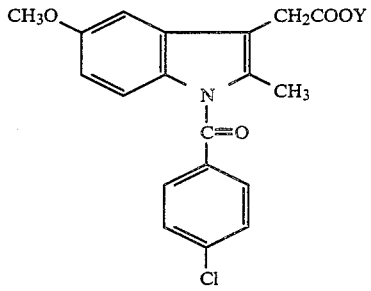

wherein Y is hydrogen atom or a metal salt, and a compound of the general formula (4):

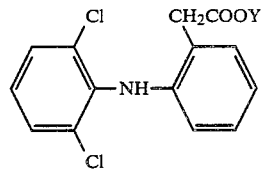

wherein Y is as defined above.

The esterification reaction employable in the present invention can be carried out by any conventional known methods and are not limited to any specific methods, but the following method is preferably employed from the viewpoint of a yield and an industrial utility; e.g. generally, in a presence of an alkaline metal carbonate such as potassium carbonate, sodium carbonate, sodium bicarbonate or potassium bicarbonate; a hydroxide of an alkaline metal such as sodium hydroxide or potassium hydroxide; a hydride of an alkaline metal such as sodium hydride, potassium hydride or lithium hydride; an organic base, for instance, a tertiary amine such as pyridine, triethylamine, N,N-dimethylaniline or tetramethylethylenediamine, or the like; an iodide of an alkaline metal such as sodium iodide or potassium iodide; a phase transfer catalyst, for instance, a crown ether such as 15-crown-5 or 18-crown-6, a cryptand such as [2,2,2]-cryptate or [2,2,2]-benzocryptate; or the like, in a non-protonic organic solvent such as N,N-dimethylformamide (hereinafter referred to as DMF), dimethylsulfoxide or hexamethylsulfonyltriamide; an organic solvent such as acetonitrile, dichloromethane, dichloroethane, chloroform, benzene, ether, acetone or tetrahydrofuran; or a mixture thereof, the reaction is carried out.

Typical examples of the metal salt of the compound of the general formula (3) or (4) usable in the present invention are, for instance, a silver salt, a copper salt, an alkaline metal salt such as lithium salt, sodium salt or potassium salt, and the like.

The reaction temperature of the esterification reaction employable in the present invention is not limited to any specific temperature range, but the reaction is preferably carried out at a temperature of 10° to 120° C.

According to the present invention, not less than 1 mole, preferably 1 to 1.5 moles of an alkylcarbonyloxyalkyl halide or an alkenylcarbonyloxyalkyl halide of the general formula (II) is advantageously used per 1 mole of a carboxylic acid residue of the general formula (3) or (4) in the esterification reaction from the economical viewpoint.

The reaction time is altered according to a used solvent, basic catalyst and reaction temperature, but the reaction is generally completed in 1 to 24 hrs.

An alkylcarbonyloxyalkylester or alkenylcarbonyloxyalkylester derivative of indolylacetic acid or anilinophenylacetic acid of the present invention prepared by the reaction condition described above is an anti-inflammatory drug of high safety, reduced remarkably an side effect such as a gastrointestinal disorder or a central nervous disturbance which is a drawback of conventional acid nonsteroidal anti-inflammatory drugs, and has an equal anti-inflammation or analgesic activity to IM and DF and an improved duration of the pharmacological activity.

Moreover, the compound of the present invention has a high fat-solubility and is superior in absorbability via mucous membrane and skin. Therefore, when an oily base is employed applicably in a pharmaceutical preparation using the compound of the present invention, the obtained drug has an advantage that it exhibits the increased pharmacological activity more rapidly and an advanced durability of the activity. In that case, the compound of the present invention is an anti-inflammatory drug capable of an advanced application.

With respect to the compound of the present invention as well as IM, DF and acemethacin, the tests for pharmacological action, acute toxicity and a rate of hydrolysis were performed. The results of the tests are shown in Table 1 and Table 2.

TABLE 1

| Test Compound | $ED_{50}$ for inhibition for carrageenan edema (mg/kg) | $LD_{50}$ for gastric ulceration (mg/kg) | Acute toxicity* $LD_{50}$ (mg/kg) | Rate of** hydrolysis (%) |
|---|---|---|---|---|
| Compound 1 | 6 | 15 | 105 | 88.9 |
| Compound 2 | 6 | 20 | 67 | 78.0 |
| Compound 3 | 6 | 15 | 65 | 97.3 |
| Compound 4 | 15 | 40 | 85 | 83.0 |
| Compound 5 | 15 | 40 | 62 | 75.3 |
| Compound 6 | 13 | 40 | 85 | 69.0 |
| Compound 7 | >20 | >20 | 780 | 60.5 |
| Compound 8 | 6 | 20 | 65 | 99.8 |
| Compound 9 | 6 | 20 | 65 | 97.3 |
| Compound 10 | 7 | 20 | 65 | 88.2 |
| Compound 11 | 15 | 10 | 45 | 85.4 |
| Compound 12 | >20 | >20 | 640 | 80.4 |
| Compound 13 | <30 | 30 | 400 | 89.7 |
| Compound 14 | <30 | 30 | 455 | 83.4 |
| Compound 15 | 20 | 50 | 500 | 80.5 |
| Compound 16 | 20 | 50 | 610 | 93.7 |
| Compound 17 | 30 | 30 | 400 | 78.4 |
| Compound 18 | 20 | 30 | 295 | 96.1 |
| Compound 19 | <30 | 30 | 380 | 86.0 |
| Compound 20 | 20 | 30 | 460 | 80.3 |
| Compound 21 | 30 | >80 | 790 | 78.2 |
| Acemethacin | 8.3 | 17.5 | 45 | 4.2 |
| IM | 5.5 | 8.0 | 31.5 | — |
| DF | 15 | 15 | 192 | — |

*mouse, oral administration
**in 1 ml of plasma rat (37° C., incubation for 1 hr)

TABLE 2

| Test Compound | Number of samples | Administered amount, orally (mg/kg) | 2 hs after the irradiation | | 3 hs after the irradiation | | 5 hs after the irradiation | |
|---|---|---|---|---|---|---|---|---|
| | | | Average ± standard error | Rate for inhibition | Average ± standard error | Rate for inhibition | Average ± standard error | Rate for inhibition |
| control | 6 | — | 2.67 ± 0.211 | — | 2.83 ± 0.167 | — | 2.83 ± 0.167 | — |
| IM | 6 | 3 | 2.17 ± 0.307 | 18.7 | 2.5 ± 0.224 | 11.7 | 2.83 ± 0.167 | 0 |
| IM | 6 | 10 | 1.33 ± 0.217** | 50.2 | 2.83 ± 0.167 | 0 | 3.0 ± 0 | 0 |
| Compound 1 | 12 | 3 | 1.50 ± 0.337** | 43.8 | 2.08 ± 0.193** | 26.5 | 1.92 ± 0.193** | 32.2 |
| Compound 1 | 12 | 10 | 1.17 ± 0.322** | 56.2 | 1.58 ± 0.288** | 44.2 | 1.92 ± 0.229** | 32.2 |
| Compound 2 | 12 | 3 | 1.83 ± 0.297** | 31.5 | 1.83 ± 0.207** | 35.3 | 2.0 ± 0.174** | 29.3 |
| Compound 2 | 12 | 10 | 0.83 ± 0.241*** | 68.9 | 0.83 ± 0.241*** | 70.7 | 1.0 ± 0.369*** | 64.7 |
| Compound 3 | 6 | 3 | 0.5 ± 0.224*** | 81.3 | 2.5 ± 0.224 | 11.7 | 2.83 ± 0.167 | 0 |
| Compound 3 | 6 | 10 | 0.67 ± 0.333*** | 74.9 | 2.3 ± 0.211 | 18.7 | 2.50 ± 0.224 | 11.7 |
| DF | 6 | 3 | 1.17 ± 0.307** | 56.2 | 2.17 ± 0.401 | 23.3 | 2.67 ± 0.211 | 5.7 |
| DF | 6 | 10 | 1.17 ± 0.307** | 56.2 | 2.50 ± 0.342 | 11.7 | 2.83 ± 0.167 | 0 |
| Compound 15 | 6 | 3 | 1.17 ± 0.167** | 56.2 | 2.0 ± 0.258* | 29.3 | 3.00 ± 0 | 0 |
| Compound 15 | 6 | 10 | 0.67 ± 0.211*** | 74.9 | 2.3 ± 0.333 | 18.7 | 2.83 ± 0.167 | 0 |
| Compound 21 | 6 | 3 | 1.33 ± 0.211** | 50.2 | 3.00 ± 0 | 0 | 3.00 ± 0 | 0 |
| Compound 21 | 6 | 10 | 1.50 ± 0.224** | 43.8 | 2.50 ± 0.224 | 11.7 | 2.50 ± 0.224 | 11.7 |

*risk rate <0.05
**risk rate <0.01
***risk rate <0.001

Anti-inflammatory action was investigated according to the method of Winter et al [cf. Pro. Soc. Exp. Biol. Med., 111, 544 (1962)] by the inhibition test of carrageenan edema employing a foot-pad edema method using carrageenan as an irritating agent and male Wister rats weighing 130 to 170 g. As is clearly seen in Table 1, the compounds of the present invention exhibit a more excellent pharmacological effect than IM and DF. Compounds 1, 2, 3, 8, 9 and 10 have an equal anti-inflammatory activity to IM and Compounds 15, 16, 18 and 20 have an almost equal anti-inflammatory activity to DF.

Gastrointestinal ulcer formation action, which is a principal side effect of an acid anti-inflammatory drug, was investigated according to the method of Okabe et al [cf. Nippon Yakurigaku Zasshi (FOLIA PHARMACOLOGICA JAPONICA), 74, 773 (1978)] as follows: Male Wister rats weighing 130 to 170 g were subjected to fasting for 24 hrs. The compounds of the present invention, IM, DF and acemethacin were suspended in 5% Tween-80 solution and administered orally 1 ml/100 g body weight to the rats, respectively. At 6 hrs after the administration, the state of glandstomach was observed by means of a dissecting microscope whether the ulcer having a diameter more than 1 mm was generated or not. As the result, the rate of ulcer generation of Compounds 1 to 6, 8 to 10, 15 to 16 and 21 was about ⅓ of that of IM and DF as clearly understood from Table 1.

Effect on central nervous system, which is another side effect of IM, was investigated according to the potentiating effect on thiopental-induced sleep in mice as follows: Male ddY mice weighing 20 to 24 g were subjected to fasting for 15 hrs. The compound 1,3 and 10, IM and DF were suspended in 5% Tween-80 solution and administered orally 1 ml/100 g body weight to the mice, respectively, while to the control was administered orally only 5% Tween-80 solution. At 30 mins after the administration, thiopental sodium was injected intravenously to each of the mice in an amount of 35 mg/l kg body weight, and then, the sleeping time was observed. When the sleeping time of the mice to which the Test Compound was administered was longer than 2 times that of the control to which only Tween-80 was administered, the given Test Compound was judged to be effective on thiopental-induced sleep potentiating effect. As the result, DF did not show the potentiating effect. With respect to Compounds 1,3 and 10, and IM, $ED_{50}$ for the potentiation of thiopental-induced sleep are shown in Table 3.

As is clearly seen in Table 3, the potentiating effect of Compounds 1,3 and 10 was 1/4.3, 1/5.7 and 1/2.5 of that of IM, respectively. Therefore, it was easily understood that the central nervous effect of the compound of the present invention was weaker than IM.

TABLE 3

| Test Compound | $ED_{50}$ for potentiation of thiopental-induced sleep (mg/kg) |
|---|---|
| Compound 1 | 455 |
| Compound 3 | 600 |
| Compound 10 | 261 |
| IM | 205 |

With respect to Compounds 1 to 3, 15 and 21 which are especially useful as an anti-inflammatory drug, IM and DF, inhibition action for ultraviolet erythema was investigated according to the method of Adames et al [cf. Nature, London, 181, 773 (1958)] using guinea pigs as follows: Male Hartley guinea pigs weighing 250 to 350 g were shaved at their sides the day before and two hrs before the ultraviolet irradiation. To the guinea pigs were administered orally Compounds 1 to 3, 15 and 21, IM and DF in amounts as described in Table 2, respectively. To the control group was administered orally only Tween-80. At 1 hr after the time of administration, the guinea pigs were irradiated at their shaved sides by ultraviolet beam for 40 seconds.

The reaction of the ultraviolet erythema was evaluated at 2 hrs, 3 hrs and 5 hrs after irradiation according to the method of Winder et al [cf. Arch. Int. Pharmacodyn., 116, 261 (1958)]. As the result, easily understood from Table 2, Compounds 3, 15 and 21 exhibit the equal inhibition effect for ultraviolet erythema to that of IM and DF. Compounds 1 and 2 show a duration of the pharmacological effect over 5 hrs, contrary to that IM has a duration of 2 hrs.

The present invention is more specifically described and explained by means of the following Examples. It is to be understood that the present invention is not limited to the Examples, and various changes and modifications may be made in the invention without departing from the spirit and scope thereof.

EXAMPLE 1

[Preparation of Compound 1]

In 30 ml of anhydrous acetonitrile was suspended 3.05 g (7.7 mmol) of potassium salt of IM. To this suspension were added 0.81 g (8 mmol) of triethylamine and 1.22 g (7.7 mmol) of potassium iodide, and then, was added 1.34 g (10 mmol) of chloromethylcrotonate with stirring at room temperature. The reaction mixture was heated to 60° C. and stirred for 5 hrs.

After cooling the reaction mixture, the insoluble materials were filtered off, and to the filtrate was added 100 ml of dietylether. The filtrate was washed with successive, a 10% aqueous solution of sodium carbonate, water and a saturated aqueous solution of sodium chloride, and dried over anhydrous magnesium sulfate. The solvent was distilled out under reduced pressure to give yellow crystals.

The crystals were recrystallized twice from a mixed solvent system of benzene and n-pentane, and 2.3 g of Compound 1 in the form of yellow crystals having a melting point of 93° to 94° C. was obtained (yield: 65.6%). The characteristic properties of the obtained Compound 1 are shown below.

Elementary analysis for $C_{24}H_{22}NO_6Cl$ (in molecular weight of 455.9): Calcd. (%): C 63.23, H 4.86. Found (%): C 63.41, H 4.87.

MMR spectrum (solvent: $CCl_4$, internal standard: TMS):

δ values (ppm)

1.79 and 1.80 (d,d, 3H, $-CH=CH-C\underline{H}_3$),
2.26 (s, 3H,

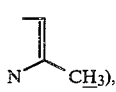

$N\quad C\underline{H}_3$), 3.47 (s, 2H,

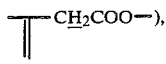

$-C\underline{H}_2COO-$), 3.63 (s, 3H, ph—$OC\underline{H}_3$),
5.43 to 5.58 (m, 1H, olefinic H),
5.52 (s, 2H,

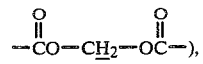

6.24 to 6.76 (m, 4H, aromatic and olefinic H),
6.99 to 7.40 (m, 4H, aromatic H)

Mass spectrum (direct injection, 20 eV):

m/e 455 (M$\ddagger$), 457 (M+2)$^+$,

312

139 [$COC_6H_4Cl$]$^+$ (base peak),
69

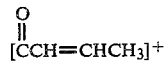

Infrared absorption spectrum ($v_{max}^{KBr}$ cm$^{-1}$): 3600 to 3300, 3100 to 2850 (aromatic and alkyl C—H), 1750 and 1740 (ester C=O), 1680 (NC=O)

EXAMPLE 2

[Preparation of Compound 2]

7.15 g (20 mmol) of IM, 50 ml of DMF and 2.76 g (20 mmol) of anhydrous potassium carbonate were mixed and stirred at 60° C. for 1 hr. To the resulting mixture was added dropwise 2.97 g (20 mmol) of distilled 3,3-dimethylacryloyloxymethylchloride, and then, the admixture was stirred at 50° to 60° C. for 3 hrs.

The obtained reaction mixture was cooled with ice, and the inorganic materials were filtered off, and then, the solvent was distilled out under reduced pressure. To the residue was added 100 ml of diethylether. The solution was washed with succesive, water, a 10% aqueous solution of sodium carbonate and a saturated aqueous solution of sodium chloride, and dried over anhydrous magnesium sulfate. The organic solvent was distilled out under reduced pressure to give 6 g of yellow crude crystals.

The crystals were recrystallized from methanol, whereby 5.7 g of Compound 2 in the form of white crystals having a melting point of 84° to 86° C. was obtained (yield: 60.8%). The characteristic properties of the obtained Compound 2 are shown below.

Elementary analysis for $C_{25}H_{24}NO_6Cl$ (in molecular weight of 469.6): Calcd. (%): C 63.88, H 5.11. Found (%): C 64.01, H 5.12.

NMR spectrum (solvent: $CCl_4$, internal standard: TMS):

δ values (ppm)

1.84 (s, 3H, olefinic —$C\underline{H}_3$),
2.12 (s, 3H, olefinic —$C\underline{H}_3$),
2.36 (s, 3H, 3.60 (s, 2H, 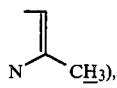

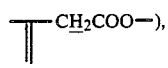

3.76 (s, 3H, ph—OCH$_3$),
5.51 to 5.54 (m, 1H, olefinic H),
5.66 (s, 2H, 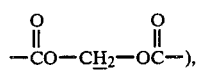

6.40 to 6.82 (m, 3H, aromatic H),
7.25 to 7.63 (m, 4H, aromatic H)
Mass spectrum (direct injection, 20 eV):
m/e
469 (M†), 471 (M+2)$^+$,
312

139 [COC$_6$H$_4$Cl]$^+$ (base peak),
83 [COCH=C(CH$_3$)$_2$]$^+$
Infrared absorption spectrum ($\nu_{max}^{KBr}$ cm$^{-1}$: 3600 to 3350, 3100 to 2850 (aromatic and alkyl C—H), 1760 and 1740 (ester C=O), 1690 (NC=O), 1650 to 1600 (C=C)

EXAMPLE 3

[Preparation of Compound 3]

The procedure of Example 2 was repeated except that there were employed 1.79 g (5 mmol) of IM, 20 ml of anhydrous DMF, 0.7 g (5 mmol) of anhydrous potassium carbonate and 0.9 g (7.5 mmol) of 2-(acetyloxy)ethylchloride to give 1.78 g of Compound 3 in the form of white crystals having a melting point of 109° to 111° C. (yield: 80.4%). The characteristic properties of the obtained Compound 3 are shown below.

Elementary analysis for C$_{23}$H$_{22}$NO$_6$Cl (in molecular weight of 443.7): Calcd. (%): C 62.26, H 4.96. Found (%): C 62.44, H 4.98.

NMR spectrum (solvent:CCl$_4$, internal standard: TMS):
δ values (ppm)
1.75 (s, 3H, 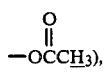

2.22 (s, 3H, 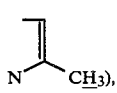

3.35 (s, 2H, 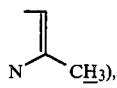

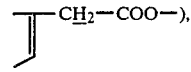

3.55 (s, 3H, ph—OCH$_3$),
3.96 (s, 4H, 

6.12 to 6.56 (m, 3H, aromatic H),
6.99 to 7.32 (m, 4H, aromatic H)
Mass spectrum (direct injection, 20 eV):
m/e
443(M†), 445 (M+2)$^+$,
312 

139 [COC$_6$H$_4$Cl]$^+$ (base peak),
131 

87 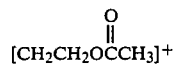

Infrared absorption spectrum ($\nu_{max}^{KBr}$ cm$^{-1}$):
3100 to 2850 (aromatic and alkyl C—H),
1765 (ester C=O),
1690 (NC=O)

EXAMPLE 4

[Preparation of Compound 4]

To 200 ml of dry acetonitrile was added 0.1 g of 18-crown-6, and the mixture was stirred at room temperature for 30 mins. To the mixture was added 3.95 g (10 mmol) of potassium salt of IM and 2.08 g (11 mmol) of 2-(crotonoyloxy)ethylchloride, and the admixture was stirred at 50° C. for 5 hrs. After cooling the reaction mixture, 200 ml of diethylether was added to the mixture. Then, the reaction mixture was worked up exactly according to the procedure described in Example 2 to give 3.15 g of purified Compound 4 in the form of pale yellow crystals having a melting point of 102° to 105° C. (yield: 67%). The Characteristic properties of the obtained Compound 4 are shown below.

Elementary analysis for C$_{25}$H$_{24}$NO$_6$Cl (in molecular weight of 469.6): Calcd. (%): C 63.88, H 5.11. Found (%): C 64.07, H 5.13.

NMR spectrum (solvent: CCl$_4$, internal standard: TMS):
δ values (ppm)
1.80 and 1.84 (d, d, 3H, olefinic —CH$_3$),
2.32 (s, 3H,

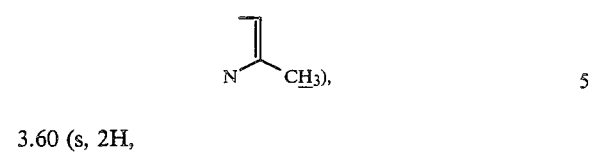

3.60 (s, 2H,

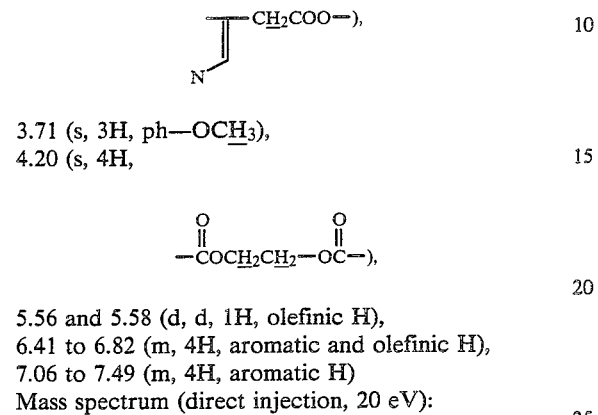

3.71 (s, 3H, ph—OC$\underline{H}_3$),
4.20 (s, 4H, 5.56 and 5.58 (d, d, 1H, olefinic H),
6.41 to 6.82 (m, 4H, aromatic and olefinic H),
7.06 to 7.49 (m, 4H, aromatic H)
Mass spectrum (direct injection, 20 eV):
m/e
  469 (M$^+$), 471 (M+2)$^+$,
  312

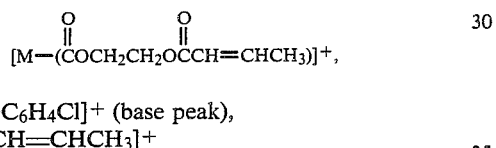

139 [COC$_6$H$_4$Cl]$^+$ (base peak),
69 [COCH=CHCH$_3$]$^+$
Infrared absorption spectrum ($\nu_{max}^{KBr}$ cm$^{-1}$): 3600 to 3350, 3100 to 2850 (aromatic and alkyl C—H), 1732 and 1720 (ester C=O), 1680 (NC=O), 1590 to 1630 (C=O)

EXAMPLE 5

[Preparation of Compound 5]

The procedure of Example 2 was repeated except that there were employed as the starting materials 3.57 g (10 mmol) of IM, 50 ml of anhydrous DMF, 1.38 g (10 mmol) of anhydrous potassium carbonate and 2.07 g (10 mmol) of 2-(3,3-dimethylacryloyloxy)ethylbromide to give 3.12 g of Compound 5 in the form of pale yellow crystals having a melting point of 87° to 90° C. (yield: 64.5%). The characteristic properties of the obtained Compound 5 are shown below.

Elementary analysis for C$_{26}$H$_{26}$NO$_6$Cl (in molecular weight of 483.9): Calcd. (%): C 64.48, H 5.37. Found (%): C 64.64, H 5.38.

NMR spectrum (solvent: CCl$_4$, internal standard: TMS):
δ values (ppm)
  1.80 (s, 3H, olefinic —C$\underline{H}_3$),
  2.02 (s, 3H, olefinic —C$\underline{H}_3$),
  2.27 (s, 3H,

3.44 (s, 2H,

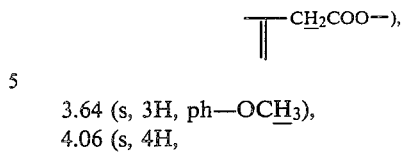

3.64 (s, 3H, ph—OC$\underline{H}_3$),
4.06 (s, 4H,

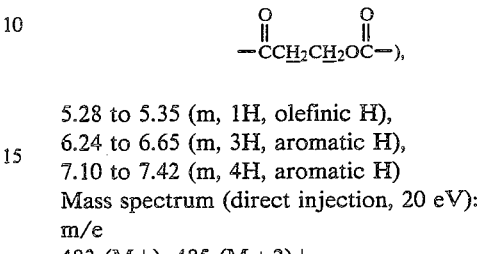

5.28 to 5.35 (m, 1H, olefinic H),
6.24 to 6.65 (m, 3H, aromatic H),
7.10 to 7.42 (m, 4H, aromatic H)
Mass spectrum (direct injection, 20 eV):
m/e
  483 (M$^+$), 485 (M+2)$^+$,
  312

139 [COC$_6$H$_4$Cl]$^+$ (base peak),
83 [COCH=C(CH$_3$)$_2$]$^+$
Infrared absorption spectrum ($\nu_{max}^{KBr}$ cm$^{-1}$):
3600 to 3350, 3100 to 2850 (aromatic and alkyl C—H), 1735 and 1715 (ester C=O), 1680 (NC=O), 1655 to 1595 (C=C).

EXAMPLE 6

[Preparation of Compound 6]

The procedure of Example 2 was repeated except that there were employed as the starting materials 1.47 g (4 mmol) of IM, 10 ml of anhydrous DMF, 0.6 g (4 mmol) of anhydrous potassium carbonate and 0.9 g (4.1 mmol) of 2-(2,4-hexadienoyloxy)ethylbromide to give 1.1 g of Compound 6 in the form of yellow crystals having a melting point of 145° to 148° C. (yield: 55.4%). The characteristic properties of the obtained Compound 6 are shown below.

Elementary analysis for C$_{27}$H$_{26}$NO$_6$Cl (in molecular weight of 496): Calcd. (%): C 65.32, H 5.24. Found (%): C 65.55, H 5.26.

NMR spectrum (solvent: CCl$_4$, internal standard: TMS):
δ values (ppm)
  1.85 (d, 3H, olefinic —C$\underline{H}_3$),
  2.36 (s, 3H,

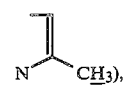

3.64 (s, 2H,

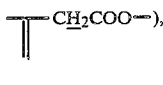

3.80 (s, 3H, ph—OC$\underline{H}_3$),
4.28 (s, 4H,

), 5.55 and 5.70 (d, 1H, olefinic H),
6.03 to 6.12 (m, 2H, olefinic H),
6.59 to 6.88 (m, 4H, aromatic and olefinic H),
7.32 to 7.61 (m, 4H, aromatic H)
Mass spectrum (direct injection, 20 eV):
m/e
495 (M$^+$), 497 (M+2)$^+$,
312

,

139 [COC$_6$H$_5$Cl]$^+$ (base peak),
95 [COCH=CH—CH=CHCH$_3$]$^+$
Infrared absorption spectrum ($\nu_{max}^{KBr}$ cm$^{-1}$): 3600 to 3350, 3050 to 2850 (aromatic and alkyl C—H), 1730 and 1715 (ester C=O), 1675 (NC=O), 1640 to 1580 (C=O)

EXAMPLE 7

[Preparation of Compound 7]

The procedure of Example 2 was repeated except that there were employed as the starting materials 3.57 g (10 mmol) of IM, 20 ml of anhydrous DMF, 1.38 g (10 mmol) of anhydrous potassium carbonate and 2.75 g (10 mmol) of 2-(3,7-dimethyl-2,6-octadienoyloxy)ethylbromide to give 3.59 g of Compound 7 in the form of pale yellow crystals having a melting point of 76° to 78° C. (yield: 65.1%). The characteristic properties of the obtained Compound 7 are shown below.

Elementary analysis for C$_{31}$H$_{34}$NO$_6$Cl (in molecular weight of 551.8): Calcd. (%): C 67.42, H 6.16. Found (%): C 67.55, H 6.18.

NMR spectrum (solvent: CCl$_4$, internal standard: TMS):
δ values (ppm)
1.57 and 1.65 (s, s, 6H, olefinic terminal —C$\underline{H}_3$×2),
2.12 (m, 7H, olefinic —C$\underline{H}_3$,

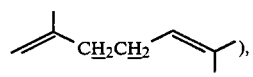), 2.37 (s, 3H,

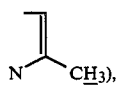), 3.68 (s, 2H,

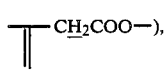), 3.79 (s, 3H, ph—OC$\underline{H}_3$),
4.24 (s, 4H,

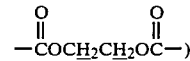)

4.90 to 5.12 (m, broad, 1H, olefinic H),
5.54 (s, 1H, olefinic H),
6.50 to 6.86 (m, 3H, aromatic H),
7.32 to 7.60 (m, 4H, aromatic H)
Mass spectrum (direct injection, 20 eV):
m/e
551 (M$^+$), 553 (M+2)$^+$,
312

[M—(COCH$_2$CH$_2$OCCH=C(CH$_3$)CH$_2$CH$_2$CH=C(CH$_3$)$_2$)]$^+$,

151 [COCH=CH(CH$_3$)CH$_2$CH$_2$CH=C(CH$_3$)$_2$]$^+$,
139 [COC$_6$H$_5$Cl]$^+$ (base peak),
Infrared absorption spectrum ($\nu_{max}^{KBr}$ cm$^{-1}$): 3600 to 3350, 3070 to 2870 (aromatic and alkyl C—H), 1725 and 1715 (ester C=O), 1675 (NC=O), 1645 to 1600 (C=C).

EXAMPLE 8

[Preparation of Compound 8]

The procedure of Example 2 was repeated except that there were employed as the starting materials 1.79 g (5 mmol) of IM, 20 ml of anhydrous DMF, 0.7 g (5 mmol) of anhydrous potassium carbonate and 1.02 g (7.5 mmol) of 1-(acetyloxy)ethylchloride, and that the obtained product was purified by means of a silica gel column chromatography to give 1.12 g of Compound 8 in the form of yellow oil (yield: 50.6%). The characteristic properties of the obtained Compound 8 are shown below.

Elementary analysis for C$_{23}$H$_{22}$NO$_6$Cl (in molecular weight of 443.9): Calcd. (%): C 62.23, H 5.00. Found (%): C 63.39, H 5.02.

NMR spectrum (solvent: CCl$_4$, internal standard: TMS):
δ values (ppm)
1.38 (d, 3H, —CH—C$\underline{H}_3$),
1.83 (s, 3H,

), 2.21 (s, 3H,

), 3.38 (s, 2H,

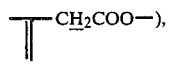), 3.60 (s, 3H, ph—OC$\underline{H}_3$),
6.23 to 6.56 (m, 4H, aromatic 3H, —C$\underline{H}$—CH$_3$),
7.07 to 7.36 (m, 4H, aromatic H)
Mass spectrum (direct injection, 20 eV):
m/e
443 (M$^+$), 445 (M+2)$^+$,

312

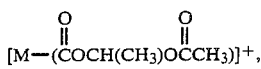

139 [COC$_6$H$_4$Cl]$^+$ (base peak),
43 [COCH$_3$]$^+$
Infrared absorption spectrum ($\nu_{max}^{neat\ (NaCl)}$ cm$^{-1}$):
  3100 to 2850 (aromatic and alkyl C—H),
  1765 (ester C=O),
  1690 (NC=O)
Refractive index (n$_D^{27}$): 1.5895

EXAMPLE 9

[Preparation of Compound 9]

The procedure of Example 7 was repeated except that there were employed as the starting materials 3.57 g (10 mmol) of IM, 50 ml of anhydrous DMF, 1.38 g (10 mmol) of anhydrous potassium carbonate and 2.0 g (15 mmol) of 1-(propionyloxy)ethylchloride to give 3.29 g of Compound 9 in the form of yellow oil (yield: 72.0%). The characteristic properties of the obtained Compound 9 are shown below.

Elementary analysis for C$_{24}$H$_{24}$NO$_6$Cl (in molecular weight of 457.9): Calcd. (%): C 62.95, H 5.28. Found (%): C 63.14. H 5.30.

NMR spectrum (solvent: CCl$_4$, internal standard: TMS):
δ values (ppm)
  0.99 (t, 3H, —COCH$_2$C$\underline{H}_3$),
  1.40 (d, 3H,

2.10 (q, 2H, —COC$\underline{H}_2$CH$_3$),
  2.23 (s, 3H,

3.39 (s, 2H,

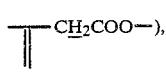

3.60 (s, 3H, ph—OC$\underline{H}_3$),
  6.22 to 6.58 (m, 4H, aromatic 3H,

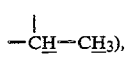

6.98 to 7.36 (m, 4H, aromatic H)
Mass spectrum (direct injection, 20 eV):
m/e
  457 (M$^+$), 459 (M+2)$^+$,
  312

139 [COC$_6$H$_4$Cl]$^+$ (base peak),
57 [COC$_2$H$_5$]$^+$
Infrared absorption spectrum ($\nu_{max}^{neat\ (NaCl)}$ cm$^{-1}$):
  3100 to 2850 (aromatic and alkyl C—H),
  1765 (ester C=O),
  1690 (NC=O)
Refractive index (n$_D^{27}$): 1.5817

EXAMPLE 10

[Preparation of Compound 10]

The procedure of Example 2 was repeated except that there were employed as the starting materials 2.5 g (7 mmol) of IM, 15 ml of anhydrous DMF, 1 g (7.2 mmol) of anhydrous potassium carbonate and 1.04 g (7 mmol) of 1-(crotonoyloxy)ethylchloride to give 1.7 g of Compound 10 in the form of yellow crystals having a melting point of 72° to 75° C. (yield: 51.7%). The characteristic properties of the obtained Compound 10 are shown below.

Elementary analysis for C$_{25}$H$_{24}$NO$_6$Cl (in molecular weight of 469.6): Calcd. (%): C 63.94, H 5.15. Found (%): C 64.04, H 5.18.

NMR spectrum (solvent: CCl$_4$, internal standard: TMS):
δ values (ppm)
  1.48 (d, 3H,

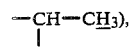

1.82 and 1.80 (d, d, 3H, olefinic —C$\underline{H}_3$),
  2.32 (s, 3H,

3.57 (s, 2H,

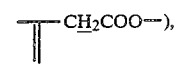

3.73 (s, 3H, ph—OC$\underline{H}_3$),
  5.60 to 5.76 (m, 1H, olefinic H),
  6.46 to 6.76 (m, 5H, aromatic 3H, olefinic H,

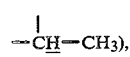

7.30 to 7.64 (m, 4H, aromatic H)
Mass spectrum (direct injection, 20 eV):
m/e
  469 (M$^+$), 471 (M+2)$^+$,
  312

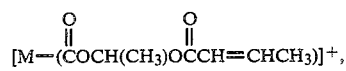

139 [COC$_6$H$_4$Cl]$^+$ (base peak),
69 [COCH=CHCH$_3$]$^+$
Infrared absorption spectrum ($\nu_{max}^{neat\ (NaCl)}$ cm$^{-1}$):
  3100 to 2850 (aromatic and alkyl C—H),
  1750 (ester C=O), 1690 (NC=O),
1630 to 1590 (C=O)

EXAMPLE 11

[Preparation of Compound 11]

The procedure of Example 2 was repeated except that there were employed as the starting materials 3.57 g (10 mmol) of IM, 20 ml of anhydrous DMF, 1.38 g (10 mmol) of anhydrous potassium carbonate and 2.43 g (15 mmol) of 1-(3,3-dimethylacryloyloxy)ethylchloride to give 3.1 g of Compound 11 in the form of yellow crystals having a melting point of 85° to 87° C. (yield: 64.1%). The characteristic properties of the obtained Compound 11 are shown below.

Elementary analysis for $C_{26}H_{26}NO_6Cl$ (in molecular weight of 483.6): Calcd. (%): C 64.58, H 5.42. Found (%): C 64.77, H 5.44.

NMR spectrum (solvent: CCl$_4$, internal standard: TMS):

δ values (ppm)

1.49 (d, 3H,

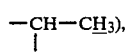

1.92 (s, 3H, olefinic —CH$_3$),
2.10 (s, 3H, olefinic —CH$_3$),
2.36 (s, 3H,

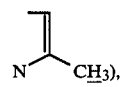

3.58 (s, 2H,

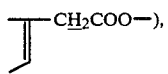

3.78 (s, 3H, ph—OCH$_3$),
5.53 to 5.62 (m, 1H, olefinic H),
6.45 to 6.87 (m, 4H, aromatic 3H,

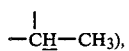

7.34 to 7.72 (m, 4H, aromatic H)

Mass spectrum (direct injection, 20 eV):

m/e 483 (M+), 485 (M+2)+,
312

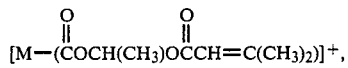

139 [COC$_6$H$_4$Cl]+ (base peak),
83 [COCH=C(CH$_3$)$_2$]+

Infrared absorption spectrum ($\nu_{max}^{KBr}$ cm$^{-1}$):
3050 to 2850 (aromatic and alkyl C—H),
1750 (ester C=O),
1675 (NC=O),
1650 to 1600 (C=C)

EXAMPLE 12

[Preparation of Compound 12]

The procedure of Example 2 was repeated except that there were employed as the starting materials 3.57 g (10 mmol) of IM, 30 ml of anhydrous DMF, 1.38 g (10 mmol) of anhydrous potassium carbonate and 1.74 g (10 mmol) of 1-(2,4-hexadienoyloxy)ethylchloride to give 3.2 g of Compound 12 in the form of yellow crystals having a melting point of 125° to 129° C. (yield: 64.6%). The characteristic properties of the obtained Compound 12 are shown below.

Elementary analysis for $C_{27}H_{26}NO_6Cl$ (in molecular weight of 495.6): Calcd. (%): C 65.44, H 5.29. Found (%): C 65.64, H 5.31.

NMR spectrum (solvent: CCl$_4$, internal standard: TMS):

δ values (ppm)

1.49 (d, 3H,

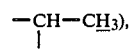

1.85 (d, 3H, olefinic —CH$_3$),
2.36 (s, 3H,

3.64 (s, 2H,

3.80 (s, 3H, ph—OCH$_3$),
5.63 (d, 1H, olefinic H),
6.03 to 6.12 (m, 2H, olefinic H),
6.54 to 6.88 (m, 5H, aromatic 3H, olefinic H,

7.32 to 7.61 (m, 4H, aromatic H)

Mass spectrum (direct injection, 20 eV):

m/e 495 (M+), 497 (M+2)+,
312

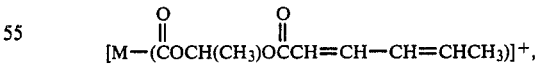

139 [COC$_6$H$_4$Cl]+ (base peak),
95 [COCH=CH—CH=CHCH$_3$]+

Infrared absorption spectrum ($\nu_{max}^{KBr}$ cm$^{-1}$):
3450, 3100 to 2850 (aromatic and alkyl C—H),
1753 (ester C=O), 1680 (NC=O),
1650 to 1600 (C=C)

EXAMPLE 13

[Preparation of Compound 13]

2.96 g (10 mmol) of DF was dissolved in 25 ml of anhydrous DMF, and to the solution was added 1.64 g (20 mmol) of sodium bicarbonate, and then, the mixture was stirred at room temperature for 1 hr. To the resulting mixture, was added dropwise 1.74 g (13 mmol) of crotonoyloxymethylchloride, and the mixture was stirred at 50° C. for 2 hrs.

After cooling the reaction mixture with ice, the inorganic materials were filtered off and the solvent was distilled out. To the residue was added 50 ml of diethylether, and the solution was washed with succesive, water, a saturated aqueous solution of sodium hydrogencarbonate and a saturated aqueous solution of sodium chloride, and then, dried over anhydrous magnesium sulfate. The solvent was distilled out to give an orange oily substance. The thus obtained substance was purified by means of a silica gel column chromatography (silica gel: 40 g of Kieselgel 60F made by MERCK & CO., INC.; eluent:benzene) to give 2.5 g of Compound 13 in the form of an orange oil (yield: 63.9%). The characteristic properties of the obtained Compound 13 are shown below.

Elementary analysis for $C_{19}H_{17}NO_6Cl$ (in molecular weight of 394.2): Calcd. (%): C 57.91, H 4.35. Found (%): C 58.05, H 4.36.

NMR spectrum (solvent: CCl$_4$, internal standard: TMS):
δ values (ppm)
1.90 and 1.93 (d, d, 3H, olefinic —C$\underline{H}_3$),
3.78 (s, 2H, ph—C$\underline{H}_2$—COO—),
5.65 to 5.84 (m, 1$\underline{H}$, olefinic H),
5.75 (s, 2H,

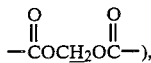

6.41 to 7.24 (m, 9H, aromatic and olefinic H, ph—N$\underline{H}$—)
Mass spectrum (direct injection, 20 eV):
m/e
393 (M$\underline{+}$), 395 (M+2)$^+$,
69 [COCH=CHCH$_3$]$^+$ (base peak)
Infrared absorption spectrum ($\nu_{max}^{neat\ (NaCl)}$ cm$^{-1}$): 3350 (N—H), 3100 to 2850 (aromatic and alkyl C—H), 1745 (ester C=O), 1660 (C=C)
Refractive index (n$_D^{27}$): 1.5810

EXAMPLE 14

[Preparation of Compound 14]

The procedure of Example 1 was repeated except that there were employed as the starting materials 2.54 g (8 mmol) of sodium salt of DF, 30 ml of dry acetonitrile, 0.81 g (8 mmol) of triethylamine, 1.33 g (8 mmol) of potassium iodide and 1.49 g (10 mmol) of 3,3-dimethylacryloyloxymethylchloride, and that the obtained product was purified by means of a silica gel column chromatography to give 1.63 g of Compound 14 in the form of an orange oil (yield: 50%). The characteristic properties of the obtained Compound 14 are shown below.

Elementary analysis for $C_{20}H_{19}NO_4Cl_2$ (in molecular weight of 408.3): Calcd. (%): C 58.83, H 4.69. Found (%): C 59.00, H 4.70.

NMR spectrum (solvent: CCl$_4$, internal standard: TMS):
δ values (ppm)
1.82 (s, 3H, olefinic —C$\underline{H}_3$),
2.06 (s, 3H, olefinic —C$\underline{H}_3$),
3.64 (s, 2H, ph—C$\underline{H}_2$—COO—),
5.39 to 5.46 (m, 1$\underline{H}$, olefinic H),
5.56 (s, 2H,

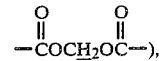

6.18 to 7.04 (m, 8H, aromatic H, ph—N$\underline{H}$—)
Mass spectrum (direct injection, 20 eV):
m/e
407 (M$\underline{+}$), 409 (M+2)$^+$,
83 [COCH=C(CH$_3$)$_2$]$^+$ (base peak)
Infrared absorption spectrum ($\nu_{max}^{neat\ (NaCl)}$ cm$^{-1}$): 3350 (N—H), 3100 to 2850 (aromatic and alkyl C—H), 1740 (ester C=O), 1660 (C=C)
Refractive index (n$_D^{27}$): 1.5815

EXAMPLE 15

[Preparation of Compound 15]

The procedure of Example 12 was repeated except that there were employed as the starting materials 2.96 g (10 mmol) of DF, 35 ml of anhydrous DMF, 1.38 g (10 mmol) of anhydrous potassium carbonate and 2.0 g (13 mmol) of distilled 2,4-hexadienoyloxymethlchloride to give 1.89 g of Compound 15 in the form of white crystals having a melting point of 87° to 89° C. (yield: 45%). The characteristic properties of the obtained Compound 15 are shown below.

Elementary analysis for $C_{21}H_{19}NO_4Cl_2$ (in molecular weight of 420.3): Calcd. (%): C 60.01, H 4.56. Found (%): C 60.19, H 4.57.

NMR spectrum (solvent: CCl$_4$, internal standard: TMS):
δ values (ppm)
1.88 (d, 3H, olefinic —C$\underline{H}_3$),
3.78 (s, 2H, ph—C$\underline{H}_2$—COO—),
5.67 (d, 1H, olefinic H),
5.72 (s, 2H,

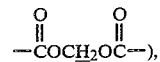

6.05 to 6.12 (m, 2H, olefinic H),
6.40 to 7.23 (m, 9H, aromatic and olefinic H, pH—N$\underline{H}$—).
Mass spectrum (direct injection, 20 eV):
m/e
419 (M$\underline{+}$), 421 (M+2)$^+$,
95 [COCH=CH—CH=CHCH$_3$]$^+$ (base peak)
Infrared absorption spectrum ($\nu_{max}^{KBr}$ cm$^{-1}$): 3330 (N—H), 3100 to 2850 (aromatic and alkyl C—H), 1740 (ester C=O), 1645 (C=C)

EXAMPLE 16

[Preparation of Compound 16]

The procedure of Example 13 was repeated except that there were employed as the starting materials 2.96 g (10 mmol) of DF, 25 ml of anhydrous DMF, 1.38 g (10 mmol) of anhydrous potassium carbonate and 1.83 g (15 mmol) of 2-(acetyloxy)ethylchloride to give 1.9 g of Compound 16 in the form of a yellow oil (yield: 49.7%). The characteristic properties of the obtained Compound 16 are shown below.

Elementary analysis for $C_{18}H_{17}NO_4Cl_2$ (in molecular weight of 382.1): Calcd. (%): C 56.58, H 4.45. Found (%): C 56.75, H 4.46.

NMR spectrum (solvent: $CCl_4$, internal standard: TMS):

δ values (ppm)

1.86 (s, 3H,

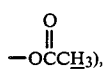), 3.59 (s, 2H,

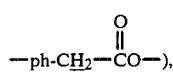), 4.03 (s, 4H,

), 6.16 to 7.0 (m, 8H, aromatic H, pH—N<u>H</u>—ph)

Mass spectrum (direct injection, 20 eV):

m/e 381 (M$^+$), 383 (M+2)$^+$,

87

(base peak),

43 $[COCH_3]^+$

Infrared absorption spectrum ($\nu_{max}^{neat\ (NaCl)}$ cm$^{-1}$): 3350 (N—H), 3100 to 2850 (aromatic and alkyl C—H), 1743 (ester C=O), Refractive index ($n_D^{27}$): 1.5747

EXAMPLE 17

[Preparation of Compound 17]

The procedure of Example 4 was repeated except that there were employed as the starting materials 2.23 g (7 mmol) of sodium salt of DF, 50 ml of anhydrous acetonitrile, 0.1 g of 18-crown-6 and 1.47 g (7 mmol) of 2-(3,3-dimethylacryloyloxy)ethylbromide, and that the obtained product was purified according to the procedure described in Example 13 to give 1.92 g of Compound 17 in the form of an orange oil (yield: 65.2%). The characteristic properties of the obtained Compound 17 are shown below.

Elementary analysis for $C_{21}H_{21}NO_4Cl_2$ (in molecular weight of 422.3): Calcd. (%): C 59.73, H 5.01 Found (%): C 59.88, H 5.03

NMR spectrum (solvent: $CCl_4$, internal standard: TMS):

δ values (ppm)

1.84 (s, 3H, olefinic —C<u>H</u>$_3$),
2.10 (s, 3H, olefinic —C<u>H</u>$_3$),
3.76 (s, 2H, ph—C<u>H</u>$_2$—$\overline{C}OO$—),
4.26 (s, 4H,

5.53 to 5.62 (m, 1H, olefinic H),
6.41 to 7.26 (m, 8H, aromatic H, ph—N<u>H</u>—)

Mass spectrum (direct injection, 20 eV):

m/e 421 (M$^+$), 423 (M+2)$^+$,

127

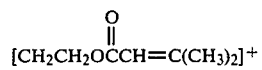

(base peak),

83 $[COCH=C(CH_3)_2]^+$

Infrared absorption spectrum ($\nu_{max}^{neat\ (NaCl)}$ cm$^{-1}$): 3350 (N—H), 3100 to 2850 (aromatic and alkyl H), 1725 (ester C=O), 1655 (C=C)

Refractive index ($n_D^{27}$): 1.5716

EXAMPLE 18

[Preparation of Compound 18]

The procedure of Example 13 was repeated except that there were employed as the starting materials 2.96 g (10 mmol) of DF, 25 ml of anhydrous DMF, 1.86 g (20 mmol) of sodium hydrogencarbonate and 1.83 g (15 mmol) of 1-(acetyloxy)ethylchloride to give 2.57 g of Compound 18 in the form of a red oil (yield: 67.2%). The characteristic properties of the obtained Compound 18 are shown below.

Elementary analysis for $C_{18}H_{17}NO_4Cl_2$ (in molecular weight of 382.1): Calcd. (%): C 56.58, H 4.45. Found (%): C 56.69, H 4.47.

NMR spectrum (solvent: $CCl_4$, internal standard: TMS):

δ values (ppm)

1.39 (d, 3H,

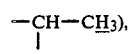

1.84 (s, 3H,

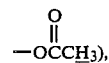

3.58 (s, 2H,

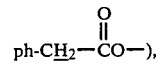

6.16 to 7.0 (m, 9H, aromatic H,

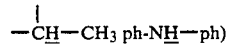

Mass spectrum (direct injection, 20 eV):

m/e 381 (M$^+$), 383 (M+2)$^+$, 277 (base peak), 43 $[COCH_3]$

Infrared absorption spectrum ($\nu_{max}^{neat\ (NaCl)}$ cm$^{-1}$): 3350 (N—H), 3100 to 2850 (aromatic and alkyl C—H), 1740 (ester C=O)

Refractive index ($n_D^{27}$): 1.5696

EXAMPLE 19

[Preparation of Compound 19]

The procedure of Example 13 was repeated except that there were employed as the starting materials 1.75 g (5.9 mmol) of DF, 25 ml of anhydrous DMF, 1.72 g (12 mmol) of sodium carbonate and 1.25 g (8.4 mmol) of 1-(crotonoyloxy)ethylchloride to give 1.2 g of Compound 19 in the form of an orange oil (yield: 49.8%). The characteristic properties of the obtained Compound 19 are shown below.

Elementary analysis for $C_{20}H_{19}NO_4Cl$ (in molecular weight of 408.2): Calcd. (%): C 58.85, H 4.65. Found (%): C 59.03, H 4.66.

NMR spectrum (solvent: $CCl_4$, internal standard: TMS):
δ values (ppm)
1.51 (d, 3H,

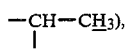

1.86 and 1.90 (d, d, 3H, olefinic —C$\underline{H}_3$),
3.73 (s, 2H, ph—C$\underline{H}_2$—COO—),
5.66 to 5.82 (m, 1H, olefinic H),
6.44 to 7.28 (m, 9H, aromatic and olefinic H, pH—N$\underline{H}$—)

Mass spectrum (direct injection, 20 eV):
m/e
407 (M$^+$), 409 (M+2)$^+$, 277 (base peak),
69 [COCH=CHCH$_3$]$^+$ Infrared absorption spectrum ($\nu_{max}^{neat\ (NaCl)}$ cm$^{-1}$): 3350 (N—H), 3100 to 2850 (aromatic and alkyl C—H), 1745 (ester C=O), 1660 (C=C)

Refractive index ($n_D^{27}$): 1.5710

EXAMPLE 20

[Preparation of Compound 20]

The procedure of Example 13 was repeated except that there were employed as the starting materials 2.96 g (10 mmol) of DF, 25 ml of anhydrous DMF, 1.38 g (10 mmol) of anhydrous potassium carbonate and 2.1 g (13 mmol) of 1-(3,3-dimethylacryloyloxy)ethylchloride to give 2.23 g of Compound 20 in the form of an orange oil (yield: 53%). The characteristic properties of the obtained Compound 20 are shown below.

Elementary analysis for $C_{21}H_{21}NO_4Cl_2$ (in molecular weight of 422.3): Calcd. (%): C 59.73, H 5.01. Found (%): C 59.88, H 5.02.

NMR spectrum (solvent: $CCl_4$, internal standard: TMS):
δ values (ppm)
1.51 (d, 3H,

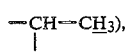

1.88 (s, 3H, olefinic —C$\underline{H}_3$),
2.11 (s, 3H, olefinic —C$\underline{H}_3$),
3.76 (s, 2H, ph—C$\underline{H}_2$COO—),
5.52 to 5.61 (m, 1H, olefinic H),
6.41 to 7.28 (m, 9H, aromatic H,

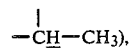

ph—N$\underline{H}$—)

Mass spectrum (direct injection, 20 eV):
m/e
421 (M$^+$), 423 (M+2)$^+$,
83 [COCH=C(CH$_3$)$_2$]$^+$ (base peak)

Infrared absorption spectrum ($\nu_{max}^{neat\ (NaCl)}$ cm$^{-1}$): 3350 (N—H), 3100 to 2850 (aromatic and alkyl C—H), 1743 (ester C=O), 1655 (C=C)

Refractive index ($n_D^{27}$): 1.5651

EXAMPLE 21

[Preparation of Compound 21]

The procedure of Example 13 was repeated except that there were employed as the starting materials 2.96 g (10 mmol) of DF, 20 ml of anhydrous DMF, 1.38 g (10 mmol) of anhydrous potassium carbonate and 2.27 g (13 mmol) of 1-(2,4-hexadienoyloxy)ethylchloride to give 1.99 g of Compound 21 in the form of an orange oil (yield: 42.9%). The characteristic properties of the obtained Compound 21 are shown below.

Elementary analysis for $C_{22}H_{21}NO_4Cl_2$ (in molecular weight of 434.2): Calcd. (%): C 60.86, H 4.84. Found (%): C 61.04, H 4.85.

NMR spectrum (solvent: $CCl_4$, internal standard: TMS):
δ values (ppm)
1.48 (d, 3H,

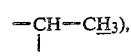

1.83 (d, 3H, olefinic —C$\underline{H}_3$),
3.64 (s, 2H, ph—C$\underline{H}_2$—COO—),
5.47 (d, 1H, olefinic H),
5.86 to 5.98 (m, 2H, olefinic H),
6.28 (d, 1H, aromatic H),
6.58 to 7.07 (m, 9H, aromatic and olefinic H,

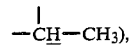

ph—N$\underline{H}$—)

Mass spectrum (direct injection, 20 eV):
m/e
433 (M$^+$), 435 (M+2)$^+$,
95 [COCH=CH—CH=CHCH$_3$]$^+$ (base peak)

Infrared absorption spectrum ($\nu_{max}^{neat\ (NaCl)}$ cm$^{-1}$): 3350 (N—H), 3100 to 2850 (aromatic and alkyl C—H), 1740 (ester C=O), 1645 (C=C)

Refractive index ($n_D^{27}$): 1.5835

In addition to the ingredients used in the Example, other ingredients can be used in the Example as set forth in the specification to obtain substantially the same results.

What we claim is:
1. A compound of the general formula (I):

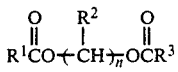

wherein $R^1$ is an anilinophenylmethyl group of the formula:

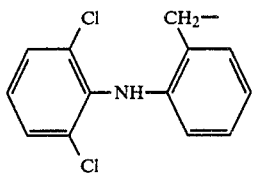

n is 1 or 2, $R^2$ is hydrogen atom or a lower alkyl group having 1 to 3 carbon atoms when n is 1, $R^2$ is hydrogen atom when n is 2 and $R^3$ is an alkyl group having 1 to 15 carbon atoms or an alkenyl group having 2 to 15 carbon atoms.

2. The compound of claim 1, Crotonoyloxymethyl-2-(2,6-dichloroanilino)-phenylacetate.

3. The compound of claim 1, 3,3-Dimethylacryloyloxymethyl-2-(2,6-dichloroanilino)phenylacetate.

4. The compound of claim 1, 2,4-Hexadienoyloxymethyl-2-(2,6-dichloroanilino)phenylacetate.

5. The compound of claim 1, 2-(Acetoxy)ethyl-2-(2,6-dichloroanilino)-phenylacetate.

6. The compound of claim 1, 2-(3,3-Dimethylacryloyloxy)ethyl-2-(2,6-dichloroanilino)phenylacetate.

7. The compound of claim 1, 1-(Acetoxy)ethyl-2-(2,6-dichloroanilino)-phenylacetate.

8. The compound of claim 1, 1-(Crotonoyloxy)ethyl-2-(2,6-dichloroanilino)phenylacetate.

9. The compound of claim 1, 1-(3,3-Dimethylacryloyloxy)ethyl-2-(2,6-dichloroanilino)phenylacetate.

10. The compound of claim 1, 1-(2,4-Hexadienoyloxy)ethyl-2-(2,6-dichloroanilino)phenylacetate.

* * * * *